United States Patent [19]

Pileski et al.

[11] Patent Number: 5,379,756
[45] Date of Patent: Jan. 10, 1995

[54] REPLACEABLE LENS ASSEMBLY FOR VIDEO LAPAROSCOPE

[75] Inventors: Michael J. Pileski, Skaneateles; Robert J. Wood, Syracuse, both of N.Y.

[73] Assignee: Welch Allyn, Inc., Skaneateles Falls, N.Y.

[21] Appl. No.: 943,930

[22] Filed: Sep. 11, 1992

[51] Int. Cl.$^6$ ............................................. A61B 1/06
[52] U.S. Cl. .................................. 128/6; 128/4; 348/65; 348/76
[58] Field of Search .............. 128/4, 6; 348/65, 76

[56] References Cited

U.S. PATENT DOCUMENTS

| | | | |
|---|---|---|---|
| 4,350,150 | 9/1982 | Kubota et al. | 128/6 |
| 4,419,987 | 12/1983 | Ogiu | 128/6 X |
| 4,856,495 | 8/1989 | Tohjoh et al. | 128/6 |
| 4,895,138 | 1/1990 | Yabe | 128/6 |
| 5,051,824 | 9/1991 | Nishigaki | 128/6 X |
| 5,156,142 | 10/1992 | Anapliotis et al. | 128/6 |
| 5,184,602 | 2/1993 | Anapliotis et al. | 128/6 |
| 5,188,094 | 2/1993 | Adair | 128/6 |

FOREIGN PATENT DOCUMENTS

| | | | |
|---|---|---|---|
| 3425166 | 1/1986 | Germany | 128/6 |
| 6266220 | 3/1987 | Japan | 128/4 |
| 0153813 | 7/1987 | Japan | 128/4 |
| 1311018 | 3/1973 | United Kingdom | 128/6 |
| 9103201 | 3/1991 | WIPO | 128/6 |

*Primary Examiner*—Richard J. Apley
*Assistant Examiner*—Karen A. Jalbert
*Attorney, Agent, or Firm*—Harris, Beach & Wilcox

[57] ABSTRACT

A video laparoscope has a miniature video camera disposed at the distal end of its insertion tube. A removably installed tubular lens cell contains one or more focussing lenses. The lens cell has a male-threaded first end and a second end on which is formed a radial flange of a predetermined diameter. A tubular lens retainer canister is fixedly mounted in the distal end of the insertion tube, and has an outer distal portion with a diameter to match the diameter of the flange. A sealing portion adjacent to this has a smaller diameter, and biases against an O-ring or similar sealing member. A female-threaded proximal portion is screwed into the male-threaded first portion of the lens cell.

11 Claims, 3 Drawing Sheets

REPLACEABLE LENS ASSEMBLY FOR VIDEO LAPAROSCOPE

BACKGROUND OF THE INVENTION

This invention relates to borescopes, endoscopes, or laparoscopes of the type in which a miniature video camera is mounted at a distal viewing head of an elongated insertion tube. The invention is more particularly concerned with an improved laparoscope improved to facilitate repair or replacement of the image-gathering optics.

Recently, the need and preference for less invasive surgical techniques has increased. Likewise, there is an increased interest in the use of video instruments for surgical applications. Video-based procedures have been proposed for minimal intervention in the patient. An example of a minimally invasive video instrument is a laparoscope for performing surgery in the abdominal cavity, where the instrument is inserted through a small incision. Other, narrow probes can be used in eye surgery. Further examples are found in industrial probes, i.e., borescopes for inspection of equipment such as boilers or steam generators, or jet engine rotors where non-destructive penetration of the equipment is necessary.

Traditional optical laparoscopes require an elongated lens tube which employs an objective lens at the distal end an ocular or eyepiece at the proximal end, and a complex series of relay lenses to carry the visual image from the objective to the ocular. For laparoscope of modest to large size, discrete lenses are used for the relay lenses. For very small diameter probes, rod lenses can be used. In either case, the relay lenses are both high-cost items, and at the same time quite delicate. For example, if the lens tube is dropped or struck, some portion of the lens system can easily shatter. If this happens, the lens tube must be replaced, at a cost of several thousands of dollars. Consequently, the industry has sought ways to reduce the risk of breakage, either by making the laparoscope more rugged or by reducing the costs of repair or replacement. However, this goal has been elusive with traditional optical scopes.

A video laparoscope with a light source based on a small, low-power metal halide discharge lamp is described in copending patent application Ser. No. 07/780,762, filed Oct. 22, 1991, and having a common assignee. As described in that patent application, a laparoscope or other similar probe has a miniature video camera that incorporates a miniature electronic imager and a lens assembly which are disposed either at the distal tip or at a proximal end of a insertion tube. For insertion tubes of about 5 mm or larger, the camera can be distally mounted. For very slim insertion tube, the camera can be proximally mounted, with a relay lens system being contained in the insertion tube. The insertion tube can be rigid or can have its tip portion articulatable. The small video camera can be incorporated in an add-on camera attachment for laparoscope having a proximal viewing port.

Disposing the camera at the distal tip of the insertion tube reduces the amount of focussing and relay lenses to be carried in the tube. This reduces the vulnerability of the lens system and also means less light is lost in the lens system. The amount of optical fiber bundle needed for illumination is reduced, which also permits the insertion tube to be made narrower.

The insertion tube proximal end is coupled through a flexible cable or umbilical to a connector module that plugs into a socket in a processor unit. A video cable that extends through the insertion tube and umbilical has terminals in the connector module that supply the video signal from the miniature camera signal to a full color or monochrome monitor. An image of a target area, such as a tissue within a patient's body cavity, can be viewed on the monitor.

Also within the processor is a high illuminance, but low-wattage light source in the form of one or more metal halide discharge lamps. These can preferably be of the type described in copending U.S. patent application Ser. Nos. 07/484,166, filed Feb. 23, 1990; 07/636,743, 07/636,744, each filed Dec. 31, 1990, and which have an assignee in common herewith. The lamp typically operates at a power of about 20 watts, and has an efficacy of at least 35 lumens per watt. The light produced, which can be controlled by the selection of salts employed, the dosage of mercury, and mechanical structure of the lamps, has an emission spectrum in the visible band, with very little radiation produced in the infrared band. Also, the arc gap of this lamp is small, which produces a small spot of light when focused onto the fiber optic bundle used for illumination. The small spot size allows all the light energy to be directed into the proximal end of a very small fiber bundle.

OBJECTS AND SUMMARY OF THE INVENTION

It is an object of this invention to provide an improved laparoscope that avoids the problems of the prior art.

It is another object to provide a laparoscope whose insertion tube includes a replaceable lens module to permit rapid repair of the laparoscope at minimal cost, without sacrifice of quality.

In accordance with an aspect of this invention, a laparoscope or similar probe has a miniature video camera incorporated into its insertion tube. The camera includes a miniature electronic imager and a focussing lens assembly. A fiber optic bundle carries light for illuminating the target and emits light from the distal end of the probe.

In a preferred embodiment, the laparoscope has a plug-in module containing the required video processing electronics to provide a video signal to a monitor, so that the target can be viewed on-screen.

The camera assembly which is disposed at the distal tip of the insertion tube has a lens assembly that is removable and replaceable. A tubular lens cell contains the one or more focusing lenses and has a male threaded first end and a second end on which there is an annular radial flange of a predetermined diameter. A sealing portion of the lens cell is disposed between the first and second ends.

The small solid state video imager chip is contained in a receptacle portion at one end of a lens retainer into which the lens cell is removably fitted. An example of a miniature camera is described in commonly assigned U.S. patent appl'n. Ser. No. 07/735,269, filed Jul. 24, 1991. The lens retainer is a tubular canister which is fixedly mounted within the distal tip of the insertion tube. Preferably, the optical fibers for illumination are positioned in an arc in the annulus defined between the lens retainer canister and the insertion tube wall. The interior of the lens retainer is formed with an outer distal recessed portion of an internal diameter that matches the flange diameter of the lens cell. A sealing portion adjacent the outer portion is of a smaller diameter and serves to bias against sealing means, such as O-rings, which are disposed on the corresponding sealing portion of the lens cell. A female threaded portion proximally of the sealing portion receives the male threaded first end of the lens cell. Then proximally of this is the imager receptacle portion which contains the imager. The outer end flange of the lens cell includes keying means to permit it to be rotated for installation or removal. In a preferred embodiment, this can include a pair of diametrically opposed recesses to receive a spanner wrench or similar device.

The above and many other objects, features, and advantages of this invention will present themselves to those skilled in the art upon reading the ensuing description of a preferred embodiment, which should be read in conjunction with the accompanying Drawing.

DETAILED DESCRIPTION OF THE PREFERRED EMBODIMENT

Figure 1:
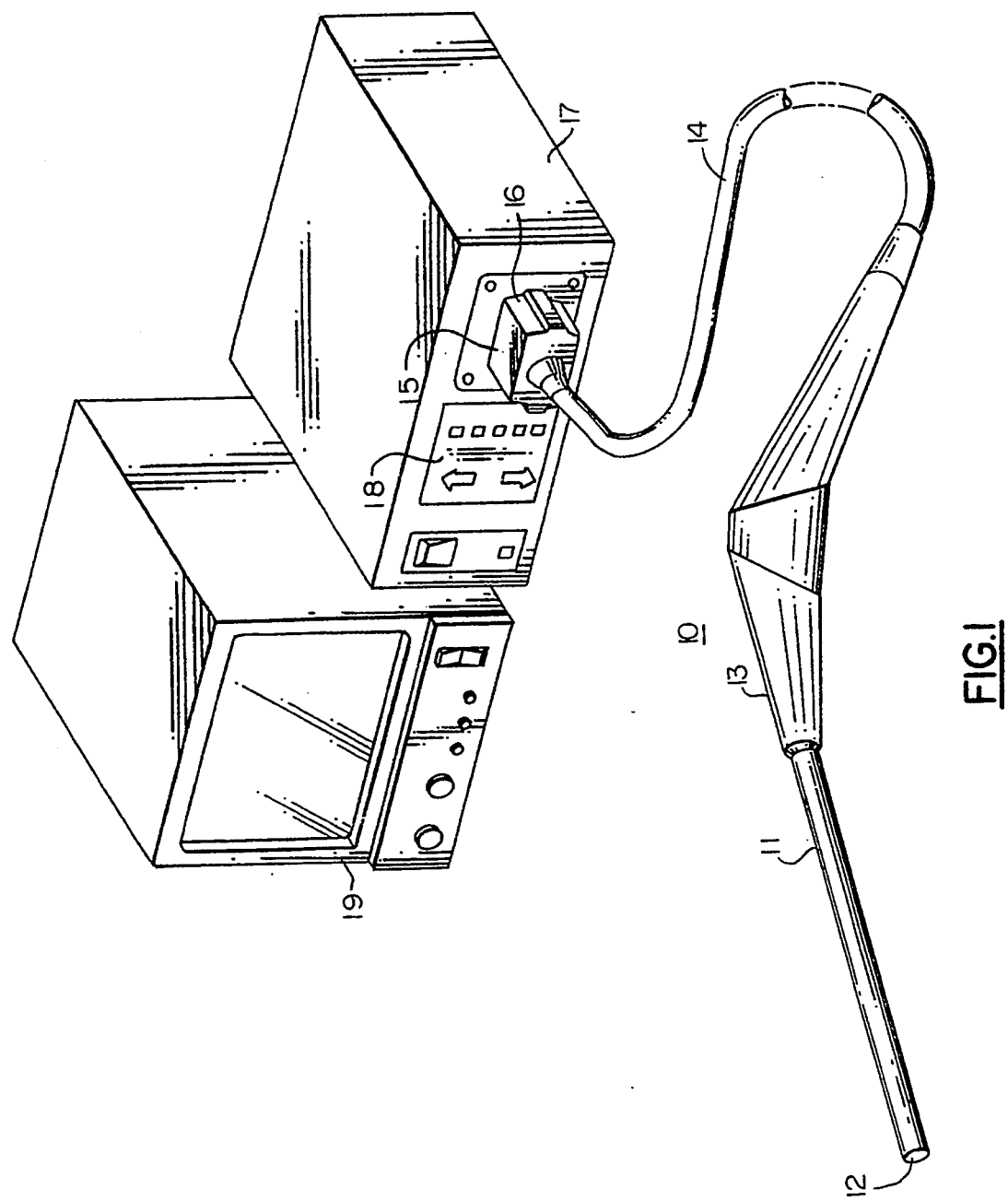
FIG. 1 is a perspective view of a laparoscope assembly which incorporates an embodiment of this invention.

With reference to the Drawing, and initially to FIG. 1, a laparoscope assembly 10 has an insertion tube 11 that is either rigid over its length or rigid with a moveable tip. The miniature video camera 12 is situated within the distal tip of the insertion tube 11. The insertion tube 11 is supported in a handle member 13, which is in turn coupled through an umbilical tube 14 to a plug-in connector module 15. The latter contains electronic circuitry that provides appropriate power levels as well as control and synchronizing signals to the video camera 12 and also receives an image signal therefrom, which it uses to produce a video signal for supplying to a video monitor. The connector module 15 inserts into a socket 16 of a lighting and power supply unit 17. Disposed on the front panel of the unit is a control panel 18, with various controls and indicators. A video monitor 19 provides a video picture of the target as viewed by the camera 12.

Figure 2:
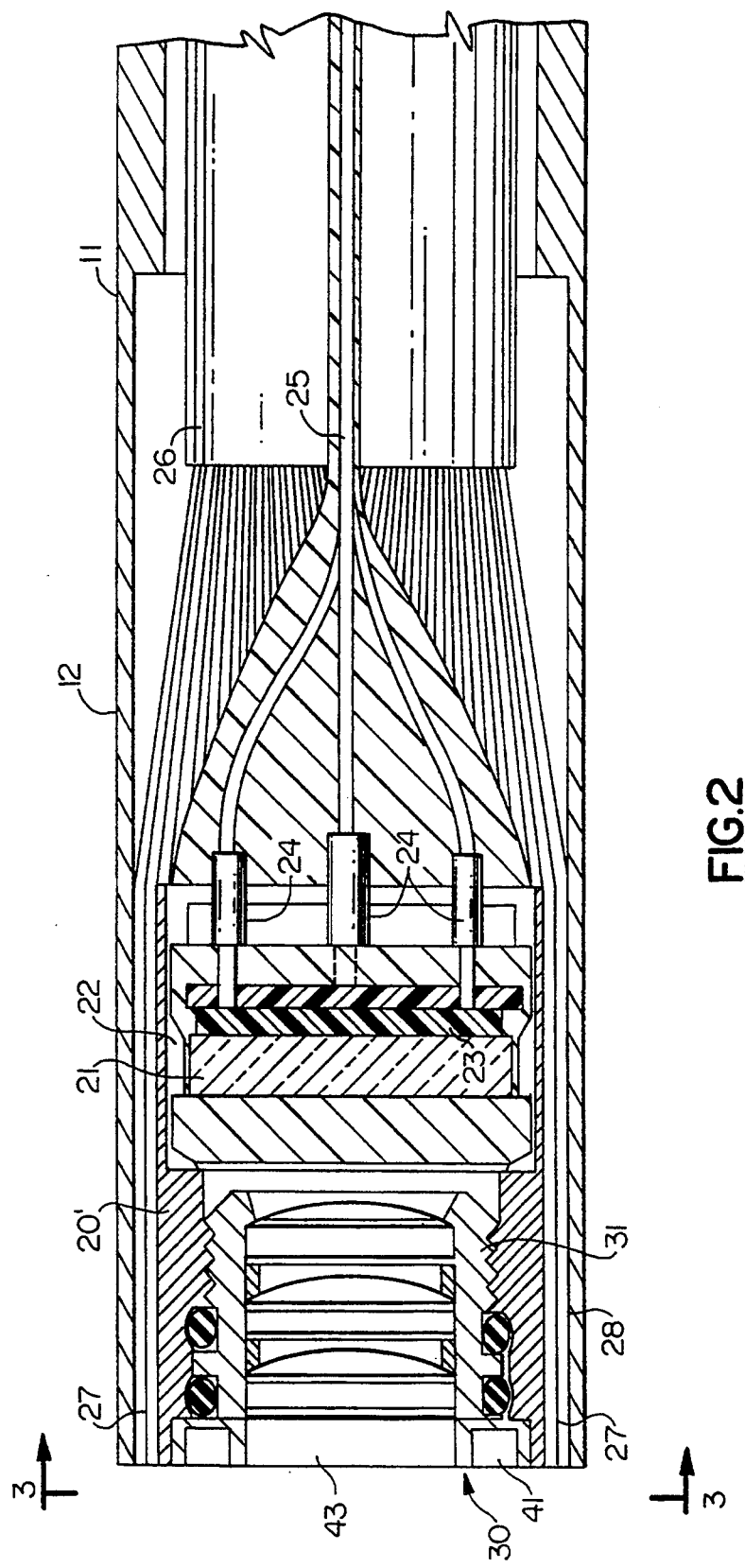
FIG. 2 is a sectional view of the camera assembly of the laparoscope of FIG. 1, showing the replaceable lens cell.
Figure 3:
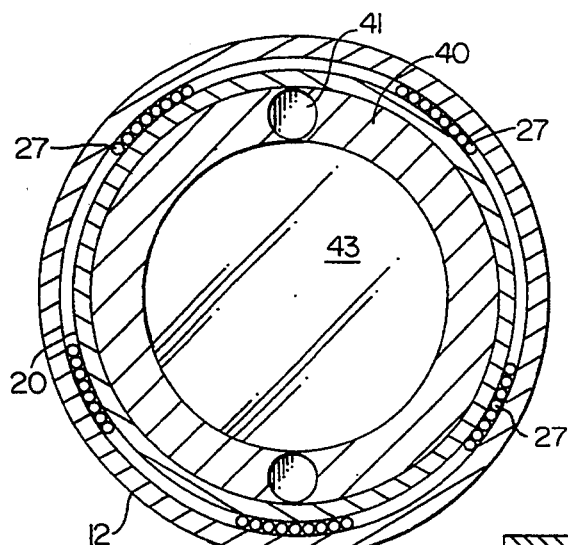
FIG. 3 is an end view taken at 3—3 of FIG. 2.
Figure 5:
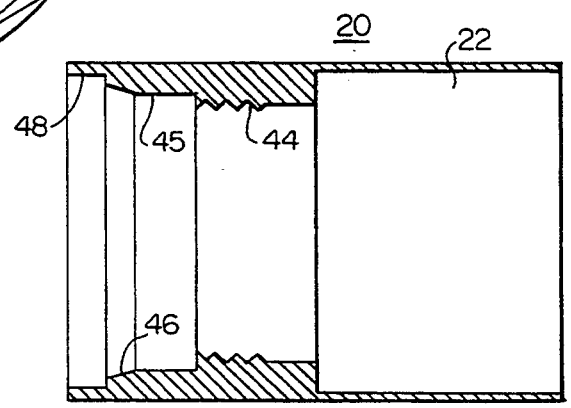
FIG. 5 is a sectional view of the lens retainer of this embodiment.
Figure 4:
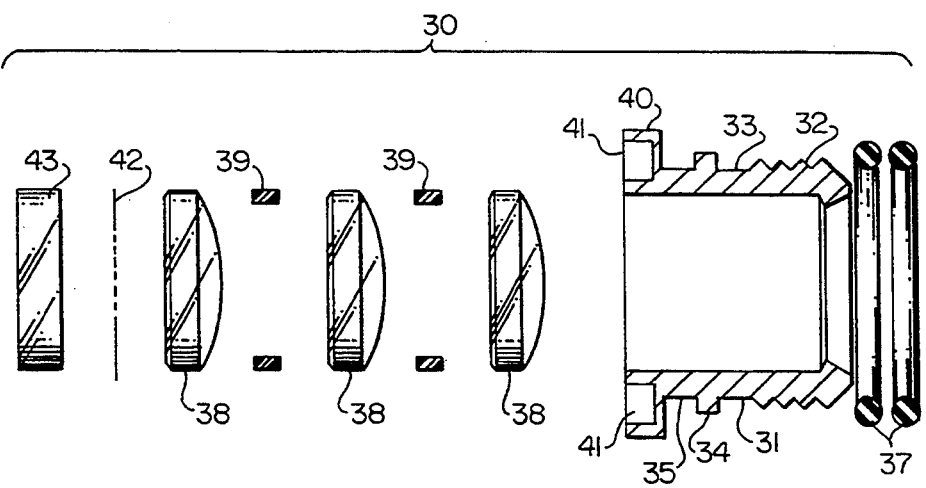
FIG. 4 is an exploded sectional view of the lens cell of this embodiment.

As shown in greater detail in FIG. 2, as well as in the remaining FIGS. 3-5, the camera 12 features a lens receptor canister 20 which is generally tubular, and which contains and supports a miniature video imager unit 21. The latter can be generally as described in U.S. Pat. No. 4,998,182. The imager 21 is situated within an proximal, wide imager receptacle portion 22 of the canister 20.

The imager 21 has a photosensitive image plate 23 located within the body of the imager, and a number of conductive terminal pins 24 that bring power and synchronizing signals, for example, to the integrated circuitry within the imager 21, and which also provide an output image signal therefrom. A number of conductors 25 are respectively joined to the pins 24, and extend proximally, back through the insertion tube 11, handle 13 and umbilical 14 to the circuitry within the connector module 15.

A pair of fiber optic light conduits 26 each contain a multiplicity of individual optical fibers 27 which are fanned out and arranged in an arc disposed in the annular space between the lens retainer 20 and the cylindrical wall 28 of the insertion tube.

As shown with additional reference to FIG. 4, the lens cell 30 is generally in the form of a tubular threaded member 31 with male threads 32 disposed at one end, and with an annular groove 33, an annular land 34 and another annular groove 35 disposed between the male thread 32 and the forward or distal end of the member 31. A pair of O-ring seals 37 are disposed in the annular grooves 33 and 35. In this embodiment there are three focussing lens 38 which are separated by respective annular spacers 39. A flange 40 protrudes radially outward at the distal end of the member 31, and has a pair of recesses 41 formed therein to receive the prongs of a spanner wrench (not shown) or similar tool. An aperture plate 42 having a fixed f-stop is positioned in advance of the outermost one of the lenses 38, and an outer flat glass plate 43, i.e. a plano-plano lens, fits into the distal end of the lens cell 30, and is preferably cemented into place.

As shown with additional reference to FIG. 5, the lens retainer 20 has a female threaded portion 44 which receives the male thread 32 of the tubular threaded member 31. A generally cylindrical sealing zone 45 adjacent to the portion 44 serves to compress against the two sealing members 37, and a tapered funnel portion 46 assists in the compression of the O-ring seals 37 when the lens cell 30 is installed into the lens retainer 20. There is also an annular cutout 48 at the distal end of the lens retainer 20, and this cutout has an inside diameter that is substantially equal to the outside diameter of the flange 40. The flange 40 fits rather closely within this cutout.

With this invention, the lens cell 30 can be changed out and replaced in a minute or less, being replaced with a similar lens cell. These lens cells 30 are comparatively inexpensive, so one or more replacement lens cells can be kept on hand without unduly increasing the cost of the instrument.

The environmental seal formed by the O-ring seals 37 permits the entire insertion tube 11 to be sterilized by immersion into a liquid or a gas sterilizing agent, such as ethylene oxide.

As shown in FIG. 3, individual optical fibers 27 form either a full circle or one or more arcs surrounding the camera assembly. The two recesses 41 in the flange 40 permits insertion of a spanner or similar wrench, to rotate the lens cell 30 for installation or removal.

With this invention, replacement of a damaged lens is relatively rapid and inexpensive. Additional spare lens cells 30 can be kept on hand, for changeover when needed. Also, various lens cells can be provided, each with a respective different f-stop in its aperture plate 42, to permit sensitivity adjustment of the laparoscope.

While this invention has been described in detail with respect to a preferred embodiment, it should be understood that the invention is not limited to that precise embodiment. Rather, many modifications and variations would present themselves to those of skill in the art without departing from the scope and spirit of this invention, as defined in the appended claims.

What is claimed is:

1. A video laparoscope which comprises an elongated insertion tube in which a camera assembly is disposed at a distal end thereof, including a focussing lens assembly for focussing the image of a target and a miniature video imager onto which said image is focussed and which produces an image signal that represents said target, a video processor connected by an umbilical to said insertion tube for furnishing control and synchronizing signals to said imager and processing the image signal therefrom to furnish a video signal suitable for a monitor to provide on-screen viewing of said target, and an optical fiber light conduit extending to a distal end of the insertion tube from which light carried by the light conduit is incident upon the target to illuminate same; and comprising the improvement wherein said lens assembly includes a removably installed tubular lens cell having a male-threaded first end and a second end on which is formed a radial flange of a predetermined diameter, and a tubular lens retainer fixedly mounted in the distal end of the insertion tube and having an outer, distal portion of an internal diameter to match the diameter of said flange, a sealing portion adjacent thereto of a smaller diameter than said outer portion, and a female-threaded proximal portion into which the male-threaded first end of the lens cell is received; and wherein said lens cell includes between said threaded first end and said flange a pair of annular grooves separated by an annular land, and a pair of resilient sealing rings situated in said grooves for sealing against the sealing portion of said lens retainer, wherein one of the grooves in which said sealing rings are situated is positioned adjacent said radial flange so as to minimize the space defined between lens cell and the lens retainer and distal of the associated sealing ring.

2. A video laparoscope according to claim 1, in which said tubular lens retainer has an imager receptacle portion proximally of said female threaded portion in which said miniature video imager is situated such that an image plane thereof is positioned at a focal plane of said one or more lenses.

3. A video laparoscope according to claim 1 wherein said sealing portion has a generally beveled portion followed by a generally cylindrical portion.

4. A video laparoscope according to claim 1 wherein said optical fiber light conduit is formed of a multiplicity of individual fibers which are fanned out and positioned in an arc against an inner wall of the insertion tube at its distal end in an annulus defined by said insertion tube and said lens retainer.

5. A video laparoscope according to claim 1 wherein said one or more lenses includes a series of focussing lenses separated from one another by annular spacers.

6. A video laparoscope according to claim 5, including a flat glass plate disposed at the distal end of said lens cell and cemented in place therein.

7. A video laparoscope according to claim 6, including an aperture plate disposed between said glass plate and said focusing lenses.

8. A video laparoscope according to claim 1, wherein said flange includes keying means to permit insertion of a tool for rotation of the lens cell relative to said lens retainer.

9. A video laparoscope according to claim 8 wherein said keying means includes a pair of diametrically opposed recesses in said flange.

10. A video laparoscope which comprises an elongated insertion tube in which a camera assembly is disposed at a distal end thereof, including a focussing lens assembly for focussing the image of a target and a miniature video imager onto which said image is focussed and which produces an image signal that represents said target, a video processor connected by an umbilical to said insertion tube for furnishing control and synchronizing signals to said imager and processing the image signal therefrom to furnish a video signal suitable for a monitor to provide on-screen viewing of said target, and an optical fiber light conduit extending to a distal end of the insertion tube from which light carried by the light conduit is incident upon the target to illuminate same; and comprising the improvement wherein said lens assembly includes a removably installed tubular lens cell having a male-threaded first end and a second end on which is formed a radial flange of a predetermined diameter, and a tubular lens retainer fixedly mounted in the distal end of the insertion tube and having an outer, distal portion of an internal diameter to match the diameter of said flange, a sealing portion adjacent thereto of a smaller diameter than said outer portion, and a female-threaded proximal portion into which the male-threaded first end of the lens cell is received, and wherein said lens cell includes between said threaded first end and said flange, and adjacent to said flange an annular groove for sealing against the sealing portion of said lens retainer, so as to minimize the space defined between the lens cell and the lens retainer and distal of said sealing ring.

11. A video laparoscope which comprises an elongated insertion tube in which a camera assembly is disposed at a distal end thereof, including a focussing lens assembly for focussing the image of a target and a miniature video imager onto which said image is focussed and which produces an image signal that represents said target, a video processor connected by an umbilical to said insertion tube for furnishing control and synchronizing signals to said imager and processing the image signal therefrom to furnish a video signal suitable for a monitor to provide on-screen viewing of said target, and an optical fiber light conduit extending to a distal end of the insertion tube from which light carried by the light conduit is incident upon the target to illuminate same; and comprising the improvement wherein said lens assembly includes a removably installed tubular lens cell having a male-threaded first end and a second end on which is formed a radial flange of a predetermined diameter, and a tubular lens retainer fixedly mounted in the distal end of the insertion tube and having an outer, distal portion of an internal diameter to match the diameter of said flange, a sealing portion adjacent thereto of a smaller diameter than said outer portion, and a female-threaded proximal portion into which the male-threaded first end of the lens cell is received, and wherein said lens cell includes between said threaded first end and said flange, and adjacent to said flange, an annular groove and a resilient sealing ring situated in said groove for sealing against the sealing portion of said lens retainer, so as to minimize the space defined between the lens cell and the lens retainer and distal of said sealing ring.

* * * * *